United States Patent
Kruger et al.

(10) Patent No.: US 6,912,415 B2
(45) Date of Patent: Jun. 28, 2005

(54) METHOD FOR ACQUIRING MRI DATA FROM A LARGE FIELD OF VIEW USING CONTINUOUS TABLE MOTION

(75) Inventors: David G. Kruger, Nelson, WI (US); Stephen J. Riederer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 282 days.

(21) Appl. No.: 09/993,120

(22) Filed: Nov. 26, 2001

(65) Prior Publication Data

US 2002/0173715 A1 Nov. 21, 2002

Related U.S. Application Data

(60) Provisional application No. 60/282,555, filed on Apr. 9, 2001.

(51) Int. Cl.[7] .................................................. A61B 5/05
(52) U.S. Cl. ........................ 600/410; 600/407; 600/413; 600/415; 600/419; 600/424; 600/428
(58) Field of Search ................................. 600/407, 410, 600/413, 419, 424, 428, 415, 411; 324/307, 318, 312, 309, 322, 300; 382/128, 133

(56) References Cited

U.S. PATENT DOCUMENTS

| | | | |
|---|---|---|---|
| 4,663,591 A | * | 5/1987 | Pelc et al. ................... 324/309 |
| 5,423,315 A | * | 6/1995 | Margosian et al. .......... 600/410 |
| 5,636,636 A | | 6/1997 | Kuhn et al. |
| 5,865,747 A | * | 2/1999 | Steckner ...................... 600/413 |
| 5,924,987 A | | 7/1999 | Meaney et al. |
| 5,928,148 A | | 7/1999 | Wang et al. |
| 6,445,181 B1 | * | 9/2002 | Pelc et al. ................... 324/307 |
| 2003/0011369 A1 | * | 1/2003 | Brittain et al. .............. 324/309 |

FOREIGN PATENT DOCUMENTS

GB      2 345 139      6/2000

OTHER PUBLICATIONS

Compensation for Effects Of Linear Motion In MR Imaging, MRM 12, 99–113 (1989), Hope W. Koring, et al.

\* cited by examiner

Primary Examiner—Brian L. Casler
Assistant Examiner—William C Jung
(74) Attorney, Agent, or Firm—Quarles & Brady LLP

(57) ABSTRACT

MRA data is acquired from a large region of interest by translating the patient through the bore of the MRI system as a three-dimensional MRA data set are acquired. Patient table movement is controlled to track a bolus of contrast agent as it passes through the region of interest. Fluoroscopic images may be acquired during the scan to enable accurate bolus tracking. A seamless image of the entire region of interest is reconstructed.

28 Claims, 5 Drawing Sheets

METHOD FOR ACQUIRING MRI DATA FROM A LARGE FIELD OF VIEW USING CONTINUOUS TABLE MOTION

CROSS-REFERENCE TO RELATED APPLICATIONS

This application is based on U.S. Provisional Patent Application Ser. No. 60/282,555 filed on Apr. 9, 2001 and entitled "Method For Acquiring MRI Data From A Large Field Of View Using Continuous Table Motion."

STATEMENT REGARDING FEDERALLY SPONSORED RESEARCH

This invention was made with government support under Grant Nos. CA37993 and HL37310 awarded by the National Institute of Health. The United States Government has certain rights in this invention.

BACKGROUND OF THE INVENTION

The field of the invention is magnetic resonance angiography ("MRA"), and particularly, studies of the human vasculature using contrast agents which enhance the NMR signals.

Magnetic resonance angiography (MRA) uses the nuclear magnetic resonance (NMR) phenomenon to produce images of the human vasculature. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals, or "views" are digitized and processed to reconstruct the image using one of many well known reconstruction techniques.

MR angiography (MRA) is the application of magnetic resonance imaging methods to the depiction of the human vasculature. To enhance the diagnostic capability of MRA a contrast agent such as gadolinium can be injected into the patient prior to the MRA scan. Excellent diagnostic images may be acquired using contrast-enhanced MRA if the data acquisition is properly timed with the bolus passage.

The non-invasiveness of MRA makes it a valuable screening tool for cardiovascular diseases. Screening typically requires imaging vessels in a large volume. This is particularly true for diseases in the runoff vessels of the lower extremity. The field of view (FOV) in MR imaging is limited by the volume of the $B_0$ field homogeneity and the receiver coil size (typically, the FOV<48 cm on current commercial MR scanners). The anatomic region of interest in the lower extremity, for example, is about 100 cm and this requires several FOVs, or stations, for a complete study. This requires that the patient be repositioned inside the bore of the magnet, the patient be re-landmarked, scout images be acquired and a preparation scan be performed for each FOV. All of these additional steps take time and, therefore, are expensive. When contrast enhanced MRA is performed, the repositioning also necessitates additional contrast injections.

Recently gadolinium-enhanced bolus chase techniques have been reported which overcome this difficulty, K. Y. Ho, T. Leiner, M. H. de Hann, J. M. A. van Engleshoven, "Gadolinium optimized tracking technique: a new MRA technique for imaging the peripheral vascular tree from aorta to the foot using one bolus of gadolinium (abs)." *Proc. 5th Meeting of ISMRM,* p203, 1997. As described in U.S. Pat. Nos. 5,924,987 and 5,928,148, MRA data is acquired from a large field of view by automatically moving the patient table to a plurality of different locations during the scan and acquiring an image at each station. The movement of the table may be timed to follow the contrast bolus through the vasculature so that peak contrast is achieved at each station.

The result of prior bolus chase MRA methods is that one ends up with a plurality of images. These are manually or automatically registered with each other to provide a single image that covers the entire extended field of view. One difficulty with this approach, however, is that the separate images have different brightnesses and/or contrasts. As a result, there are discontinuities at the boundaries of images where they have been patched together. Another difficulty with the multi-station method is that valuable time is lost when the table is moved from one station to the next. During that time no image data is being acquired and further time is lost in bringing the spin magnetization into dynamic equilibrium before image data is acquired. In a three-dimensional scan this lost data acquisition time can mean that the scanning process does not keep pace with the moving contrast bolus and some image contrast is lost in later images.

SUMMARY OF THE INVENTION

The present invention is a method for acquiring an MR image from an extended field of view in which the patient table is continuously moved during the scan. The acquired MRI data is motion corrected to a common table reference position and a single, seamless MR image is reconstructed. MRI data acquired during the scan may be used to reconstruct images in real-time that enable the operator to monitor the progress of the contrast bolus and to adjust the speed of the table motion accordingly to insure peak contrast throughout the scan.

A general object of the invention is to produce a single MR image over a field of view which exceeds the normal field of view of the MRI system. The subject is moved continuously through the MRI system and views are acquired along with table position data. Each view is position corrected using the associated table position data to produce a single array of MRI data which is used to reconstruct an image.

Another object of the invention is to better time the acquisition of MRI data with the movement of the contrast bolus through the subject. Once the scan is begun no time is wasted. For a given image resolution and pulse sequence, the table is moved continuously at the maximum possible velocity. Table velocity can be slowed as needed to remain properly aligned with peak contrast as it traverses through the subject.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

The present invention allows the subject to be imaged over a field of view (FOV) which can be many times larger than the static FOV allowed by a typical MRI scanner. The invention allows the MRI scanner to run uninterrupted while the patient table is continuously moved through the portion of the scanner volume which presents the best combination of homogeneous static magnetic field and linear magnetic field gradients. This region is typically known as the scanner's "sweet spot." The invention allows the acquisition of arbitrarily large FOVs along the table motion direction with one uninterrupted data set. Two and three-dimensional imaging are possible. The method of imaging during continuous table motion can be coupled with other techniques, including real-time MR imaging, to provide real-time control of the table motion and scan parameters. The invention is primarily directed toward MR angiography, but is also a general MRI imaging method.

Figure 3:
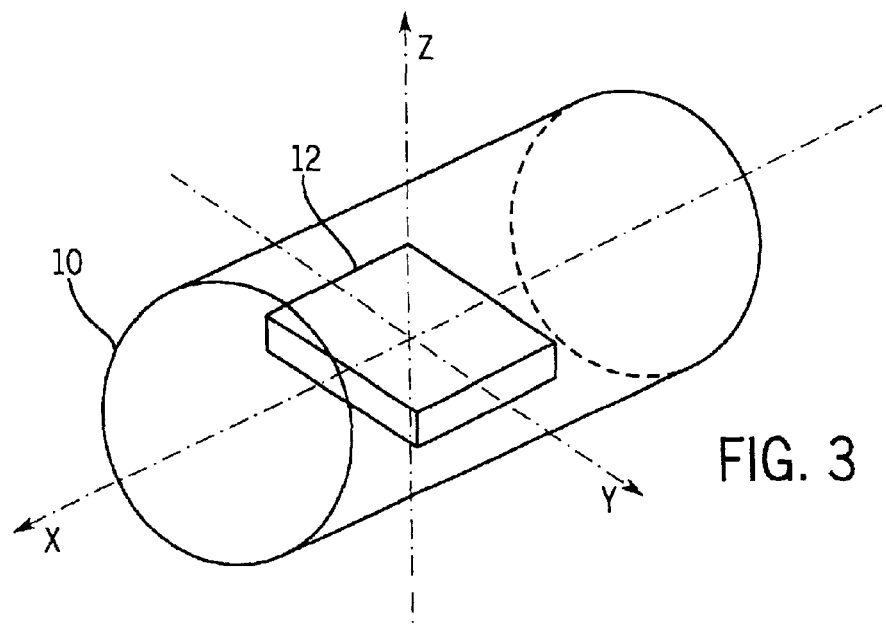
FIG. 3 is a schematic representation of an exemplary imaging volume within the bore of the MRI system of FIG. 1.

The invention can be described by referring to FIG. 3 which schematically shows the bore 10 of an MRI scanner. For this discussion a slab 12 with coronal orientation is being imaged. The readout direction (X axis) is along the direction of motion of the table and the slab select direction is along the Z axis. For 2DFT imaging, phase encoding is performed along the Y axis and for 3DFT imaging, phase encoding is performed along both the Y and Z axes.

We define $FOV_{tot}$ as the full desired field of view along the X direction and $FOV_x$ as the field of view along X for the readout of any single NMR signal. We assume that $FOV_{tot} > FOV_x$ thus necessitating the invention described here to provide an image for the full FOV if continuous table motion is desired.

As the subject is moved through the scanner along the x-axis, MRI data is acquired from the slab 12 by a series of imaging pulse sequences. During each pulse sequence the readout of the encoded k-space data is performed in the X direction. The raw k-space data is typically anti-alias filtered and subsequently sampled at a bandwidth assuming some $FOV_x$ in the readout (X) direction.

Figure 4:
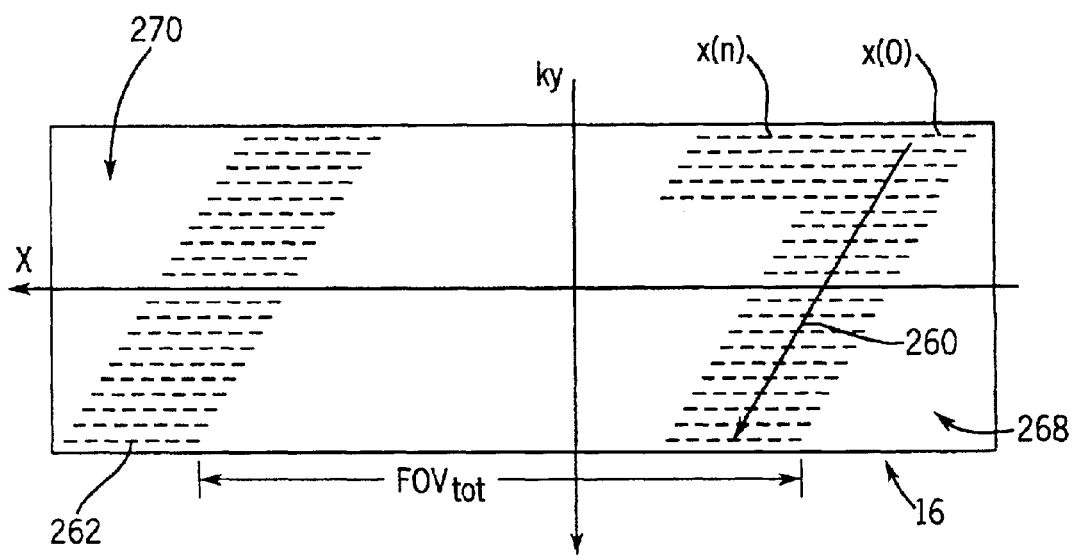
FIG. 4 is a schematic representation of a data matrix into which data acquired with the pulse sequence of FIG. 2 is stored.

Referring to FIG. 4, the raw k-space data are acquired in a series of imaging pulse sequences, a Fourier transformation (FT) is performed on each NMR signal in the readout direction and the result is placed in a matrix of memory locations 16 which represents the desired resolution in the X, Y and Z directions. This once-transformed view is a line of data placed in the matrix 16 and shifted in the X direction to a position that represents the patient position at the time the NMR echo signal was acquired. The position of the patient table relative to a reference location is known for every echo readout. The data acquisition is performed until all of the data matrix 16 is filled and the table has reached the final position. The final image is formed by Fourier transforming along the remaining Y and if 3D, the Z directions.

The following is a discussion of the theory of signal alteration due to arbitrary positioning of the patient and the adjustment of the acquired NMR echo signal. The MR signal measured during a standard image acquisition can be described by:

$$S_n(t) = \int \int m(x,y) e^{-i\gamma G_n y t_y} e^{-i\gamma G_x x t} dx dy \quad (1)$$

x is the frequency-encoding (readout) direction, y is the phase-encoding direction, $G_x$ and $G_n$ are the respective gradients, m(x,y) is the transverse magnetization of the object in spatial coordinates, $\gamma$ is the gyromagnetic ratio, and $t_y$ is the duration of the y gradient. The index n is the repetition number of the acquisition and runs from 0 to N−1 where N is the total number of phase encodings along the Y axis.

An object, shifted from its initial reference position along x some arbitrary distance has position Δ.

The signal from this shifted object is then given by:

$$\hat{S}n(t) = \int \int m(x-\Delta, y) e^{-i\gamma G_n y t_y} e^{-i\gamma G_x x t} dx dy \quad (2)$$

Now by substitution of variables $$x' = x - \Delta \text{ and } dx' = dx$$

we have $$\hat{S}_n(t) = \int \int m(x', y) e^{-i\gamma G_n y t_y} e^{-i\gamma G_x (x'+\Delta) t} dx' dy \quad (3)$$

$$\hat{S}_n(t) = e^{-i\gamma G_x \Delta t} \int \int m(x', y) e^{-i\gamma G_n y t_y} e^{-i\gamma G_x x' t} dx' dy \quad (4)$$

where $e^{-i\gamma G_x \Delta t}$ is a phase term representing the positional shift of the object in k-space. It is assumed that $\gamma$, Gn and Δ are known for any specific phase encoding. The phase factor required to recover or unshift the signal Sn(t) is then $e^{+i\gamma G_x \Delta t}$.

There are two possible methods to position each echo using the previous theory. The direct method in which the shifted data is repositioned by applying the phase factor to the continuous presampled, raw k-space data, and the time and memory efficient method in which a combination of phase shifting and positional shifting is applied to the sampled data. These are described in more detail in the description of the preferred embodiment of the invention.

DESCRIPTION OF THE PREFERRED EMBODIMENT

Figure 1:
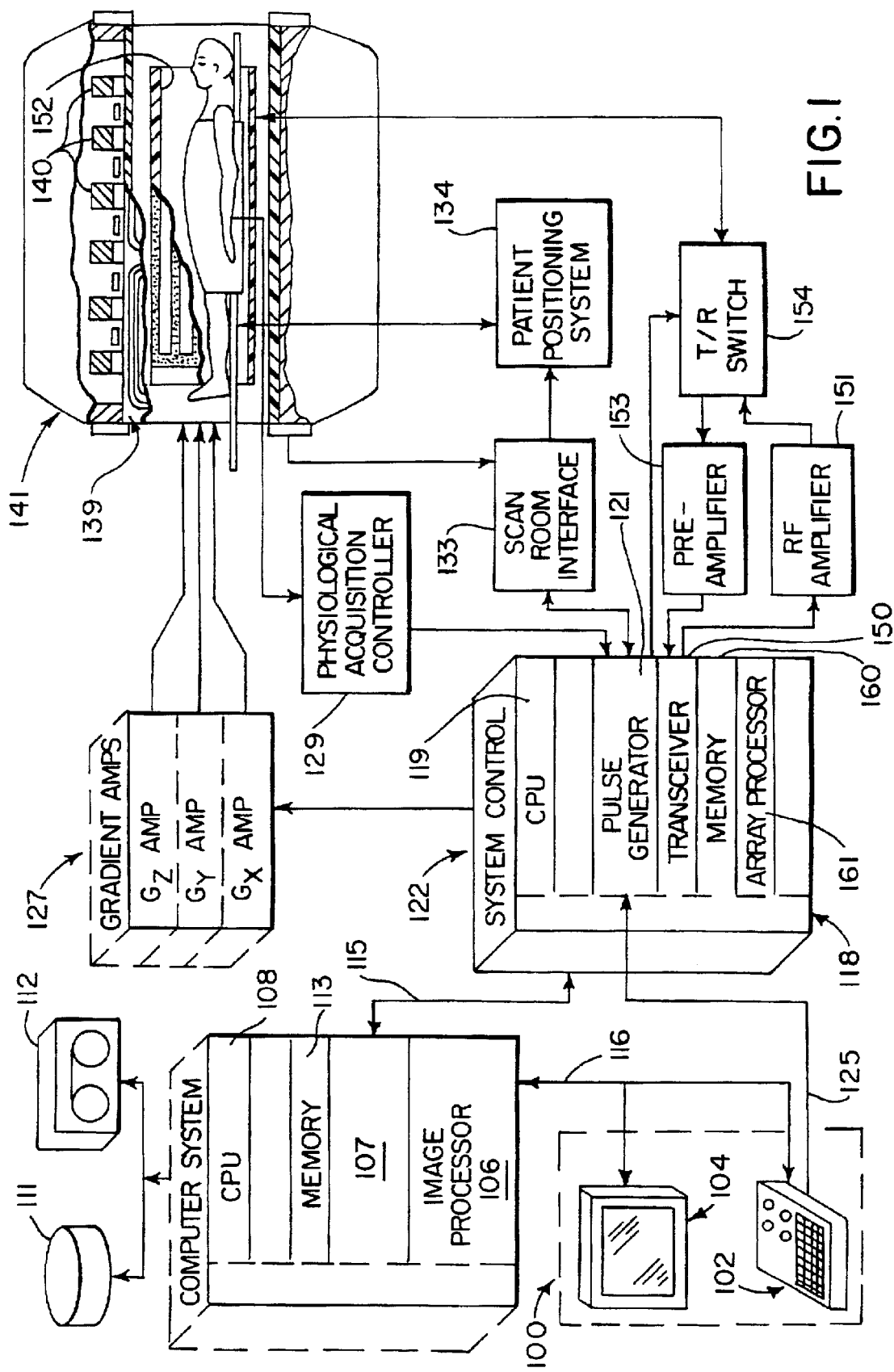
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan rom interface circuit 133 that a patient positioning system 134 receives commands from the pulse generator module 121 to move the patient through the scanner to perform the scan in accordance with the present invention. The current position of the table at any time during the scan is read into the system control 122 and is used to adjust the acquired NMR data according to the present invention as will be described in more detail below. The operator can control the operation of the patient positioning system 134 through the keyboard and control panel 102. This includes controlling the velocity of table motion during the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The NMR signals picked up by the RF local coil are digitized by the transceiver module 150 and transferred to a memory module 160 in the system control 122. An array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

Figure 2:
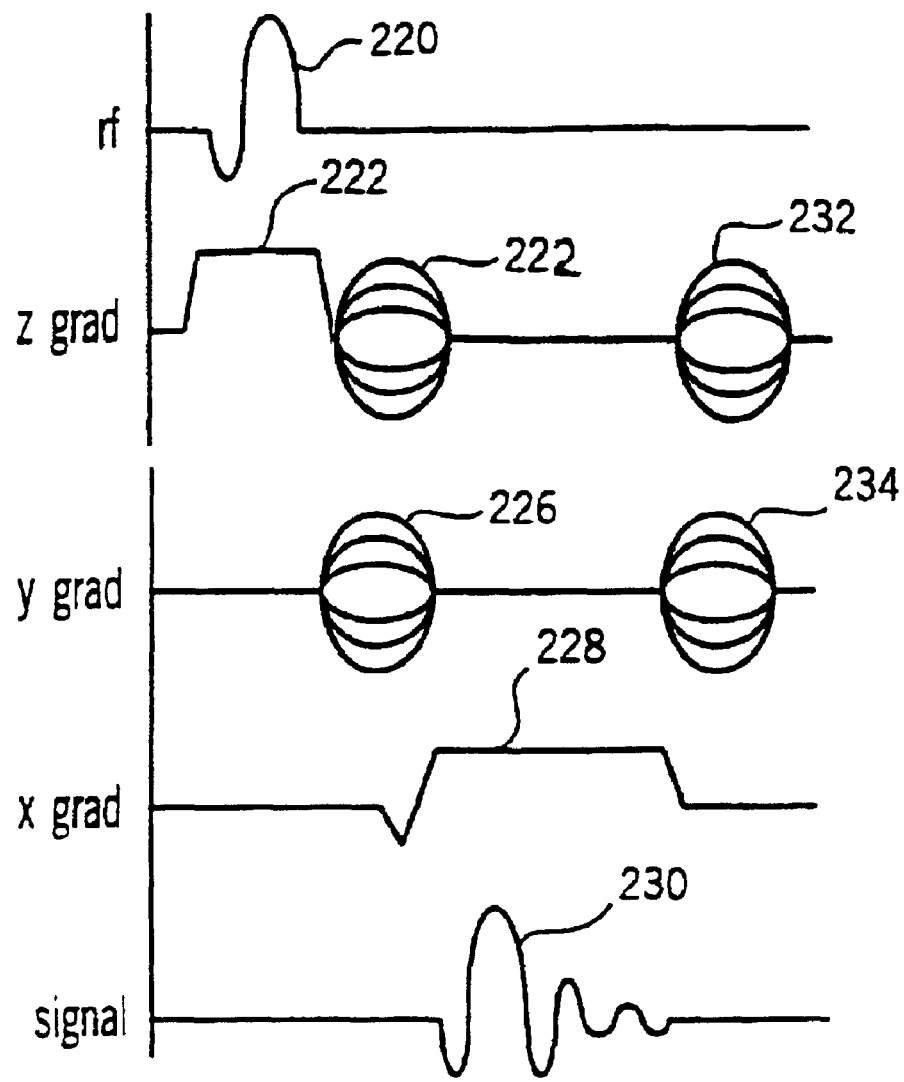
FIG. 2 is a graphic representation of a pulse sequence performed by the MRI system of FIG. 1 to practice a preferred embodiment of the invention.

While many pulse sequences may be used to practice the present invention, in the preferred embodiment a 3D gradient-recalled echo pulse sequence is used to acquire the NMR data. Referring particularly to FIG. 2, an RF excitation pulse 220 having a flip angle of 45° is produced in the presence of a slab select gradient pulse 222 to produce transverse magnetization in the 3D volume of interest as taught in U.S. Pat. No. 4,431,968. This is followed by a phase encoding gradient pulse 224 directed along the z axis and a phase encoding gradient pulse 226 directed along the y axis. A readout gradient pulse 228 directed along the x axis follows and a partial echo (60%) NMR signal 230 is acquired and digitized as described above. After the acquisition, rewinder gradient pulses 232 and 234 are applied to rephase the magnetization before the pulse sequence is repeated as taught in U.S. Pat. No. 4,665,365.

As is well known in the art, the pulse sequence is repeated and the phase encoding pulses 224 and 226 are stepped through a series of values to sample the 3D k-space in the field of view. In the preferred embodiment 32 phase encodings are employed along the z axis and 256 phase encodings are employed along the y axis. Sampling along the $k_x$ axis is performed by sampling the echo signal 230 in the presence of the readout gradient pulse 228 during each pulse sequence. It will be understood by those skilled in the art that only a partial sampling along the $k_x$ axis may be performed, and if this is done, the missing data is computed using a homodyne reconstruction or by zero filling. This enables the echo time (TE) of the pulse sequence to be shortened to 1.0 ms and the pulse repetition rate (TR) to be shortened to 4.5 ms.

Figure 5:
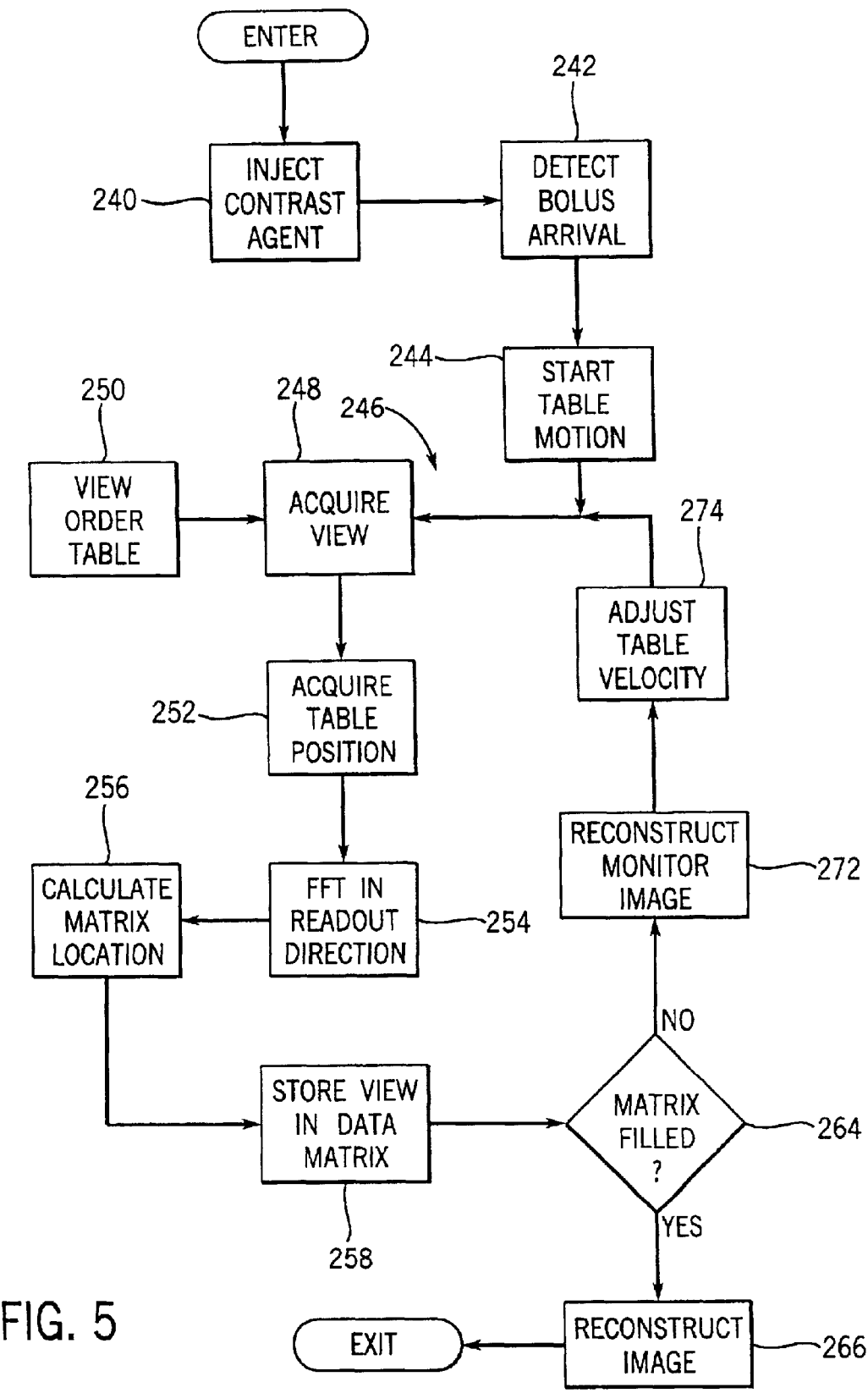
FIG. 5 is a flow chart illustrating the steps employed in practicing the preferred embodiment of the invention.

The preferred embodiment of the invention is a 3D CE-MRA scan of a subject after injection of a contrast agent. When the scan prescription is entered by the operator, scan parameters such as the imaging pulse sequence FOV and resolution are defined along all axes. Unique to the present invention, the $FOV_{tot}$ is also defined. Based on this information a data matrix 16 is defined as illustrated in FIG. 4. Referring particularly to FIG. 5, after the injection of the contrast agent at process block 240, 2D images are rapidly acquired and reconstructed to display the vasculature at the starting boundary of the $FOV_{tot}$. Arrival of the contrast bolus is detected at process block 242 by observing when the arteries brighten. At this time table movement is initiated as indicated at process block 244. There are other methods for detecting bolus arrival, including automated methods such as that described in U.S. Pat. No. 6,167,293.

A loop is then entered at 246 in which MRI data is acquired as the table moves the patient through the sweet spot of the scanner. A table reference location is also established at this time. As indicated at process block 248, a view is acquired by performing the above-described pulse sequence. Many different view orders may be employed and the prescribed view order is stored in table 250. After acquisition of the NMR echo signal, the current table position is also acquired, as indicated at process block 252, and the NMR echo signal is Fourier transformed along the x-axis as indicated at process block 254. As indicated at process block 256, the proper location in the data matrix 16 for the acquired view is then calculated and the data is stored therein as indicated at process block 258.

Figure 6:
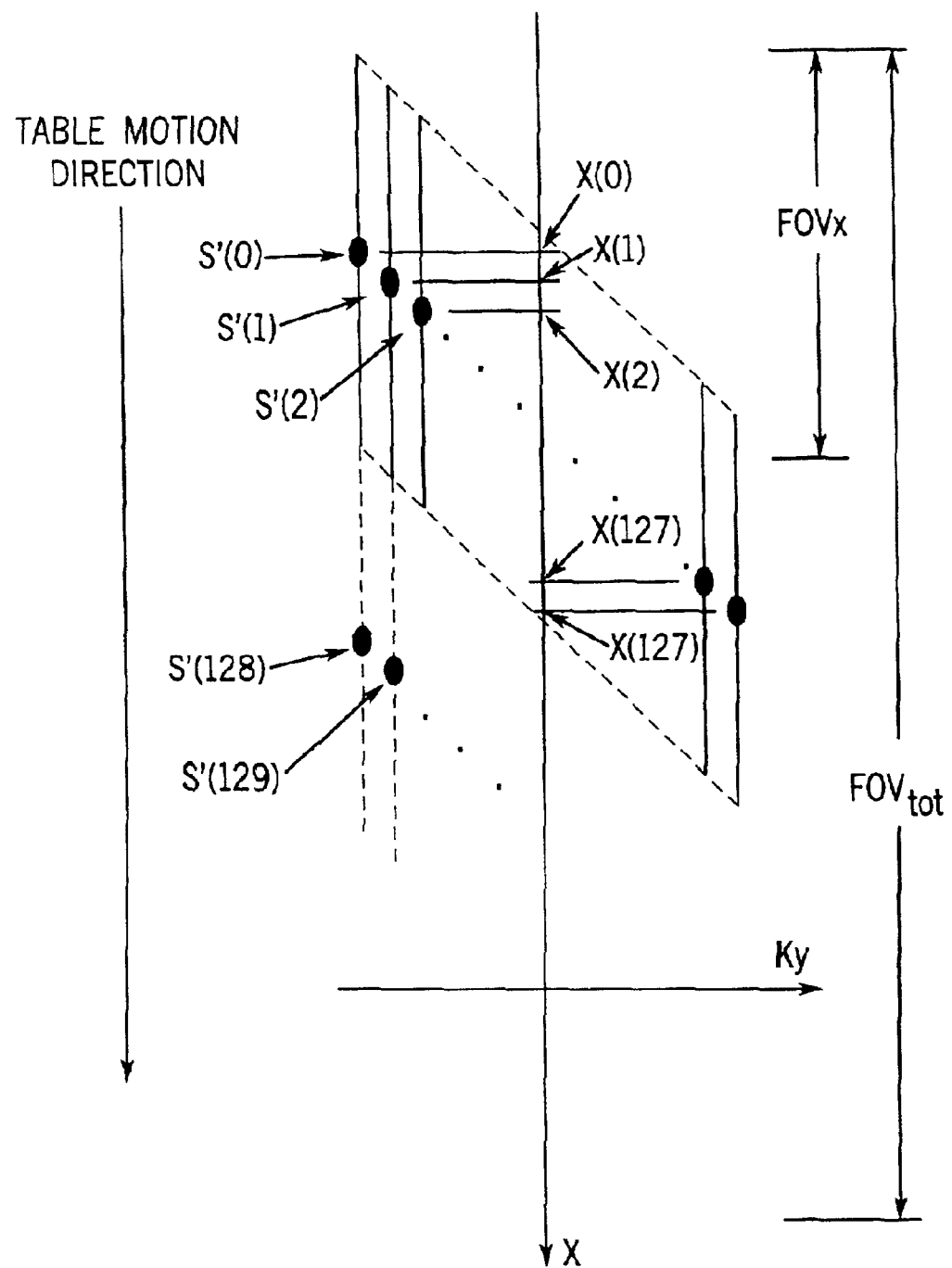
FIG. 6 is a schematic representation of how acquired data is stored in the data matrix of FIG. 4.

The location for each acquired view in the data matrix 16 is determined by two factors, the view number and the location of the patient table at the time the view was acquired. This is illustrated in FIGS. 4 and 6 for a two-dimensional acquisition with a monotonic view order. The first view is acquired at echo location x(0) which serves as a reference location. Subsequent views are acquired as the y axis phase encoding is stepped through its 128 values. The location in the data matrix 16 along its $k_y$ axis is determined by the $G_y$ phase encoding for the view. As indicated by arrow 260, the center of each successively acquired NMR echo signal after Fourier transformation along x is also shifted along the x-axis due to table movement. The amount of this shift from the reference position x(0) is measured at the time of view acquisition using an electronic spatial encoder or by using the follow equation:

$$x(n) = V_{ref} t$$

or alternatively $$x(n) = V_{ref} \cdot n \cdot TR$$

where $V_{ref}$ is the table velocity, t is the time past since the beginning of the scan, n is the number of pulse sequence repetitions since the start of the scan and TR is the time required for one pulse sequence repetition. The storage pattern is similar to a usual Cartesian k-space sampling pattern, but it is skewed by the table motion. When all the phase encoding views have been acquired, the process repeats and each new view of once transformed data is concatenated to the previous acquired $k_y$ view. It should be apparent that in a 3D acquisition a series of $k_z$ phase encoded views are also acquired at each $k_y$ phase encoding, and these are shifted and stored in a 3D data matrix 16 in the same manner.

In general, the table motion might be such that the displacement along X from one repetition to the next is not an integral number of X pixels. The data for these repetitions must be shifted with a precision of less than one pixel to maintain consistency. The displacement X(n) is known and can be split into two parts as follows:

$$X(n) = m \cdot \Delta x + \delta x(n) \quad (5)$$

where $\Delta x$ is the pixel to pixel spacing along the x-direction:

$$\Delta x = \frac{FOV_x}{N_x} = \frac{FOV_{tot}}{N_{tot}} \quad (6)$$

where $N_x$ and $N_{tot}$ are the number of pixels in the X direction for the echo readout and for the total FOV respectively. Also, m is the larger integer such that $m \cdot \Delta x < X(n)$, and $\delta(n)$ is the sub-pixel-sized remainder which forces equation (5) to hold. As before, n is the index on the pulse sequence repetition number. The actual displacement positioning consists of two steps, coarse and fine, presented here in reverse order of application for ease of understanding.

Step 2, coarse positioning: The Fourier transformed signal is shifted by m pixels as given in the first term of equation (5) and directly placed into the hybrid matrix 16 with a positional accuracy of $\Delta x$. The data then requires additional sub-pixel correction by the amount $\delta(n)$ to maintain data consistency. This process is performed in step 1.

Step 1, fine positioning: Prior to Fourier transformation in X, a phase twist representing the sub-pixel correction $\delta(n)$ is applied along the sampled echo: i.e.

$$\hat{S}_n(k_x, k_y(n)) = e^{i2\pi \frac{k_x}{N_a} \cdot \frac{\delta(n)}{\Delta x}} \cdot S_n(k_x, k_y(n)). \quad (7)$$

Fourier transformation of $\hat{S}_n$ along the x-axis followed by the coarse positioning of Step 2 yields the desired $\hat{S}_n(x, k_y, (n))$. In principle it would be possible to perform the entire displacement positioning using the phase manipulation approach of equation (7), but because multiple Fourier transformations of length $N_{tot}$ would be required for each $k_y$ value acquired, this "direct method" is not preferred because the two part position shifting and phase shifting has been found to be computationally more efficient.

It can be seen that after one complete cycle of $k_y$ phase encoding values has been completed and stored in the data matrix 16, the process repeats itself and the phase encodings are applied a second time. Depending upon the number of phase encodings and the patient table velocity, the second time a view is acquired for a specific phase encoding, the placement of the echo signal samples in the data matrix 16 along the x direction may or may not overlap with some of the echo signal samples acquired for the previous measurement at that phase encoding. In the 2D example shown in FIG. 4, such a view is shown at x(n) and the timing is such that there are no overlapping samples with the previously acquired view at x(0). In general some overlap will occur and the redundant, overlapping signal samples are averaged to improve SNR.

Referring again to FIG. 4, views are acquired and stored in the data matrix 16 until samples have been acquired for the entire extended field of view $FOV_{tot}$. The last view as indicated at 262 in FIG. 4, and after it is acquired and stored as determined at decision block 264, the scan is complete and a single image is reconstructed at process block 266 using the samples in data matrix 16. In the 3D acquisition of the preferred embodiment, this reconstruction includes Fourier transformation of the data matrix 16 along the $k_y$ and $k_z$ axes and calculation of pixel intensities from the resulting complex numbers. Typically, a two-dimensional projection image is then produced from the resulting three-dimensional array of image pixel intensities. The well-known maximum intensity pixel technique is preferred for producing the projection image and a pre-contrast mask image may also be subtracted to suppress signals from non-vascular tissues.

As shown in FIG. 4, the extended field of view $FOV_{tot}$ over which complete k-space sampling is acquired is smaller than the x axis extent over which samples are acquired. The regions 268 and 270 of partial sampling at the beginning and end of the scan can also be reconstructed to extend the total field of view, but it can be appreciated that image quality will decline as fewer samples are used in the reconstruction.

Referring again to FIG. 5, after each view is acquired and stored during the scan, data in the data matrix 16 may be employed to reconstruct a two-dimensional monitor image as indicated at process block 272. Real-time images are thus produced for the operator who can use the information therein to control the scanning process. In addition to changing the usual scan parameters, the operator can adjust the table velocity as indicated at process block 274. This might be done, for example, to better match the speed at which the contrast bolus is moving through the extended field of view $FOV_{tot}$.

The real-time 2D monitor image may be produced in a number of ways. The preferred method is to reconstruct a full maximum intensity pixel (MIP) projection through the image stack as the data is being acquired. Unlike typical static 3D image acquisitions, a partial 3D data set can be reconstructed as the hybrid matrix fills. For Nz slices and Ny phase encodes in Y, Ny Fourier transforms in the Z direction and Nz Fourier transforms in the Y direction can be performed with each TR. Each set of these described Fourier transform sets in Z and Y (including the previous transform in X) provide a partial 3D image set that is of one pixel length in the X direction. Ny pixels in the Y direction and Nz pixels in the Z direction. The maximum pixel value of a projection through this partial image set as well as earlier partial data sets can be found at the same time. The projection may be in the Z direction directly or in oblique angles through previously reconstructed partial image sets. The 2D MIP images can be displayed on the real-time monitor as each portion of the 3D data set is filled. Also, specific individual slices from the 3D data set can be viewed in real time rather than the MIP projection.

Alternatively the same process can be performed before the hybrid matrix is completely filled. No matter what phase encoding strategy is used, the phase encode order will periodically return to the center of k-space during the acquisition. Images viewed would possibly have a lower spatial resolution (in Y and Z) but would be more temporally recent than allowing full hybrid space filling.

These real-time 2D or low resolution 3D images may be used to monitor scan progress. This not only includes the physical position of the acquisition on the patient at that time but can be used to monitor the contrast bolus itself. The bolus time-position information can be used to reduce or possibly increase the velocity of the scan during the runoff study.

The table velocity to be used for the continuous motion is an independently chosen parameter. There are guidelines for its selection. In order to match table motion to the playout of phase encoding views the table should move a complete field-of-view (FOV$_x$) in the time required for application of one complete cycle of the phase encodings. At this velocity, consecutive measurements of the same view will abut and have neither an overlap nor an intervening gap along the readout x direction. We define this as the "reference table velocity", and for 2D imaging is given by:

$$V_{ref,2D} = \frac{FOV_x}{N_y \cdot TR}\left[\frac{cm}{sec}\right]$$

where N$_y$ is the number of y phase encodes and TR is the repetition time of the imaging pulse sequence. For 3D imaging in order to allow for both phase encode directions the reference table velocity is given by:

$$V_{ref,3D} = \frac{FOV_x}{N_y \cdot N_z \cdot TR}\left[\frac{cm}{sec}\right]$$

where N$_z$ is the number of z phase encodes. Note there is no dependence on the chosen resolution in X, only the chosen readout FOV$_x$. The table can be slowed or even stopped if redundant data are desired. In that case the redundant data can replace or be averaged with the non-zero data already stored in the data matrix 16.

FOV$_x$ can be variable during the scan. An acquisition can be performed with higher table velocity and thus greater temporal efficiency if a portion, or all of the hybrid space is acquired with a larger FOV$_x$. FOV$_x$ can also be reduced if a higher spatial resolution is desired for a limited region within the FOV$_{tot}$. Regardless of changes in table speed or readout FOV$_x$, a single, data matrix 16 is formed from which a seamless image of the extended field of view FOV$_{tot}$ can be reconstructed.

We have shown the feasibility of acquiring 2D and 3D images which cover longitudinal fields-of-view many times longer than the readout FOV possible in a single static image acquisition. The data for these images are acquired in conjunction with continuous table motion. This approach eliminates discontinuities in image signal at station boundaries as well as the need for overlap in FOV. The total scan times required for the moving table MRA acquisition vs. a generic fixed multi-station approach can be compared. For equal readout FOVs the continuous motion approach of the present invention provides reduced overall scan time because time dedicated to station-to-station motion and dummy repetitions is eliminated.

With the introduction of shorter bore, less claustrophobic MRI systems, the present invention provides the ability to image large longitudinal fields of view in such systems. In addition, by using one of the new fast 3D steady state pulse sequences the invention allows whole body screening with one fast exam. This can be done using targeted contrast agents which determine, for example, the extent of metastases for certain cancers or the quantitative assessment of systemic thromus.

In summary, continuously moving table acquisitions have been demonstrated for 2DFT and 3DFT MR acquisition using gradient echo and spin-echo methods. Phantom and in vivo images are sharp and appear devoid of motion artifacts as well as interference effects between consecutive FOVs. The method offers the potential for high resolution 2D and 3D MRI or extended objects.

What is claimed is:

1. In a magnetic resonance imaging (MRI) system having a defined field of view (FOV), a method for producing an image of a subject over an extended field of view (FOV$_{tot}$) which is larger than the FOV, the steps comprising:
   a) moving the subject through the MRI system such that the extended field of view (FOV$_{tot}$) passes through the defined field of view (FOV);
   b) continuously acquire NMR data from the subject as it is moved through the FOV by repeatedly performing an imaging pulse sequence which acquires NMR data comprising a view of the subject using a readout gradient directed along the direction of subject movement;
   c) adjusting each view acquired in step b) using subject position information;
   d) storing each adjusted view in a data matrix; and
   e) reconstructing an image using the data matrix.

2. The method as recited in claim 1 in which the MRI system has a table, and step a) is performed by:
   i) placing the subject on the table; and
   ii) moving the table.

3. The method as recited in claim 2 in which the table is moved continuously while performing step a).

4. The method as recited in claim 2 in which the table is moved at different velocities while performing step a).

5. The method as recited in claim 2 which includes:
   injecting the subject with a contrast agent; and
   in which the table is moved at a velocity which tracks the contrast agent as it moves through the extended field of view (FOV$_{tot}$).

6. The method as recited in claim 5 which includes:
reconstructing monitoring images during the performance of step a) from data stored in the data matrix.

7. The method as recited in claim 2 in which step c) includes adjusting the location in the data matrix in which the view is stored in step d) along the direction of subject movement as a function of the table location at the time the view is acquired in step b).

8. The method as recited in claim 2 in which step c) includes adjusting the phase of the NMR data in the view as a function of the table location at the time the view is acquired in step b).

9. The method as recited in claim 2 in which step b) further includes:
   i) acquiring table location information as each view is acquired; and
   the table location information is used in step c) to adjust each corresponding view.

10. The method as recited in claim 9 in which step c) includes:
    i) performing a Fourier transformation of the NMR data in the view; and
    ii) calculating a location in the data matrix for the transformed view as a function of the table location at the time the view was acquired in step b).

11. The method as recited in claim 1 in which step c) includes adjusting the location in the data matrix in which the view is stored in step d) along the direction of subject movement.

12. The method as recited in claim 1 in which step c) includes adjusting the phase of the NMR data in the view.

13. The method as recited in claim 1 in which step c) includes:
    i) adjusting the phase of the NMR data in the view;
    ii) Fourier transforming the phase adjusted NMR data in the view; and
    iii) adjusting the location in the data matrix in which the Fourier transformed view is stored in step d) as a function of subject location at the time the view is acquired in step b) with respect to a subject reference location.

14. The method as recited in claim 1 in which step c) includes:
    i) Fourier transforming the acquired view; and
    ii) adjusting the location in the data matrix in which the Fourier transformed view is stored in step d) as a function of subject location at the time the view is acquired in step b) with respect to a subject reference location.

15. The method as recited in claim 1 in which the data matrix is a two-dimensional array of data.

16. The method as recited in claim 1 in which the data matrix is a three-dimensional array of data.

17. In a magnetic resonance imaging (MRI) system, the improvement comprising:
    a) a table for supporting a subject and for moving the subject through a defined field of view (FOV) of the MRI system;
    b) a pulse generator for operating the MRI system under the direction of a pulse sequence to continuously acquire a series of NMR data views of the subject as the subject is moved through the FOV using a readout gradient directed along the direction of table movement;
    c) means for adjusting each acquired view as a function of subject location at the time the view is acquired with respect to a reference subject location;
    d) a memory for storing the adjusted views as a data matrix; and
    e) means for reconstructing an image from data in the data matrix which has a field of view in the direction of table motion which is larger than the defined FOV.

18. The improvement as recited in claim 17 in which element c) includes:
    i) means for Fourier transforming each acquired view; and
    ii) means for storing the Fourier transformed view in the data matrix at a location determined by the subject location at the time the view was acquired.

19. The improvement as recited in claim 17 which also includes:
    f) means for reconstructing an image from data in the data matrix as the subject is moved through the defined FOV and views are being acquired.

20. The improvement as recited in claim 19 which also includes:
    g) means for controlling the velocity of table motion as views are being acquired.

21. In a magnetic resonance imaging (MR) system having a defined field of view (FOV), a method for producing a three-dimensional image of a subject over an extended field of view ($FOV_{tot}$) which is larger than the FOV, the steps comprising:
    a) moving the subject through the MRI system such that the extended field of view ($FOV_{tot}$) passes through the defined field of view (FOV);
    b) continuously acquire NMR data from the subject as it is moved through the FOV by repeatedly performing a three-dimensional imaging pulse sequence which acquires NMR data comprising a view of the subject;
    c) adjusting each view acquired in step b) using subject position information;
    d) storing each view in a data matrix;
    e) reconstructing two-dimensional monitor images as step b) is performed using adjusted data stored in the data matrix, each reconstructed monitor image covering substantially less than the extended field of view ($FOV_{tot}$); and
    f) reconstructing an image over the extended field of view ($FOV_{tot}$) using the data matrix.

22. The method as recited in claim 21 in which the MRI system has a table, and step a) is performed by:
    i) placing the subject on the table; and
    ii) moving the table.

23. The method as recited in claim 22 which includes:
    injecting the subject with a contrast agent;
    and in which the table is moved at a velocity which tracks the contrast agent as it moves through the extended field of view ($FOV_{tot}$).

24. The method as recited in claim 23 in which table motion velocity is adjusted during the performance of steps a) and b) to better track the contrast agent as determined by the reconstructed monitor images.

25. A method for producing an image of a subject with a magnetic resonance imaging (MRI) system, the steps comprising:
    a) moving the subject through a defined field of view (FOV) of the MRI system along a motion axis;
    b) continuously acquiring NMR data from the subject as the subject is moved along said motion axis through the FOV, the NMR data being acquired by:
       i) producing an RF excitation pulse in the presence of a slab select gradient pulse to produce transverse magnetization in a three-dimensional volume having a thickness along a slab select gradient axis which is perpendicular to the motion axis;

ii) producing a phase encoding gradient pulse;

iii) acquiring an NMR signal in the presence of a readout gradient field directed along the axis of motion; and iv) repeating steps i), ii) and iii) and cycling the phase encoding gradient pulse through a set of discrete values to acquire k-space data from the excited three-dimensional volume;

c) storing the acquired k-space data in a data matrix;

d) adjusting the data stored in the data matrix to offset the effect of table motion thereon; and e) reconstructing an image from the adjusted data stored in the data matrix.

26. The method as recited in claim 25 in which step d) includes:

Fourier transforming data stored in the data matrix along the motion axis; and shifting the storage location of the Fourier transformed data in the data matrix along the motion axis.

27. The method as recited in claim 25 which includes:

recording the location of the subject as each NMR signal is acquired; and phase shifting the k-space data corresponding to each NMR signal by an amount determined by the subject location as the NMR signal was acquired.

28. The method as recited in claim 27 which includes:

Fourier transforming the k-space data corresponding to each NMR signal; and shifting the storage location in the data matrix along the axis of motion of each Fourier transformed NMR signal by an amount determined by the subject location as the NMR signal was acquired.

* * * * *

UNITED STATES PATENT AND TRADEMARK OFFICE
CERTIFICATE OF CORRECTION

PATENT NO.    : 6,912,415 B2
DATED         : June 28, 2005
INVENTOR(S)   : Kruger et al.

It is certified that error appears in the above-identified patent and that said Letters Patent is hereby corrected as shown below:

Column 4,
Line 21, "x is" should be -- where x is --.
Between Equations (3) and (4) insert -- and --.

Column 7,
Line 18, "follow" should be -- following --.
Line 50, Equation (5) should appear on line -- $x(n) = m \cdot \Delta x + \delta x(n)$ --.

Column 10,
Line 35, "MRI or extended" should be -- MRI of extended --.

Column 12,
Line 22, "(MR)" should be -- (MRI) --.

Signed and Sealed this

Fourth Day of October, 2005

JON W. DUDAS
*Director of the United States Patent and Trademark Office*